US012168028B2

(12) United States Patent
Hare et al.

(10) Patent No.: US 12,168,028 B2
(45) Date of Patent: Dec. 17, 2024

(54) METHODS FOR OBTAINING CARDIOMYOGENIC PRECURSOR CELLS (71) Applicant: UNIVERSITY OF MIAMI, Miami, FL (US)

(72) Inventors: Joshua M. Hare, Miami Beach, FL (US); Konstantinos Chatzistergos, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 982 days.

(21) Appl. No.: 16/649,522

(22) PCT Filed: Sep. 21, 2018

(86) PCT No.: PCT/US2018/052215
§ 371 (c)(1),
(2) Date: Mar. 20, 2020

(87) PCT Pub. No.: WO2019/060721
PCT Pub. Date: Mar. 28, 2019

(65) Prior Publication Data
US 2020/0246389 A1    Aug. 6, 2020

Related U.S. Application Data (60) Provisional application No. 62/562,150, filed on Sep. 22, 2017.

(51) Int. Cl.
*A61K 35/34* (2015.01)
*A61K 38/25* (2006.01)
*C12N 1/38* (2006.01)
*C12N 5/074* (2010.01)
*C12N 5/077* (2010.01)
*C12N 5/10* (2006.01)

(52) U.S. Cl.
CPC .............. *A61K 35/34* (2013.01); *A61K 38/25* (2013.01); *C12N 1/38* (2013.01); *C12N 5/0657* (2013.01); *C12N 5/0696* (2013.01); *C12N 5/10* (2013.01); *C12N 2501/415* (2013.01); *C12N 2501/60* (2013.01); *C12N 2501/85* (2013.01); *C12N 2506/45* (2013.01)

(58) Field of Classification Search
CPC .......... A61K 35/34; A61K 38/25; C12N 1/38; C12N 5/0657; C12N 5/0696; C12N 5/10; C12N 2501/415; C12N 2501/60; C12N 2501/85; C12N 2506/45
See application file for complete search history.

(56) References Cited

U.S. PATENT DOCUMENTS

2013/0209416 A1    8/2013    Ma
2013/0230921 A1    9/2013    Keller et al.
2014/0179604 A1    6/2014    Schally et al.
2015/0216911 A1    8/2015    Vines et al.
2016/0251624 A1    9/2016    Wang et al.

FOREIGN PATENT DOCUMENTS

WO    2014/114465 A1    7/2014

OTHER PUBLICATIONS

Nsair et al. Characterization and Therapeutic Potential of Induced Pluripotent Stem Cell-Derived Cardiovascular Progenitor Cells. PLoS ONE. 2012, 7(10): e45603. (Year: 2012).*
Burridge et al. Chemically defined generation of human cardiomyocytes. Nature Methods. 2014; 11(8): 855-860. (Year: 2014).*
Granata et al. Growth hormone-releasing hormone promotes survival of cardiac myocytes in vitro and protects against ischaemia-reperfusion injury in rat heart. Cardiovascular Research. 2009; 83: 303-312. (Year: 2009).*
Yang et al. Human cardiovascular progenitor cells develop from a KDR+ embryonic-stem-cell-derived population. Nature. 2008; 453 : 524-528. (Year: 2008).*
Xu et al. Somatostatin receptor type 2 contributes to the self-renewal of murine embryonic stem cells. Acta Pharmacologica Sinica. 2014; 35: 1023-1030. (Year: 2014).*
Florea et al. PNAS. 2014; 111(48): 17260-17265. (Year: 2014).*
Behrens et al., Nkx2-5 Mediates Differential Cardiac Differentiation Through Interaction with Hoxa10, Stem Cells Dev., 22(15):2211-2220 (2013).
Florea et al., Abstract 244: Cytoprotective effect of growth hormone releasing hormone agonist in cardiac stem cells, Circulation Research, 115:A244 (2014).
Fujita et al., Revolution in GPCR signalling: opioid receptor heteromers as novel therapeutic targets: IUPHAR review 10, J. Pharmacol. Sci., 171(18):4155-76 (2014).
Hatzistergos et al., cKit+ cardiac progenitors of neural crest origin, Proc. Natl. Acad. Sci., 112(42):13051-13056 (2015).
Hatzistergos et al., Ghrhr is a cell-surface market of human pluripotent stem cell-derived cardiomyogenic precursors, American Heart Association, Control/Tracking No. 2017-A-549-AHA-BCVS, 1-03 (2017).
International Application No. PCT/US2018/052215, International Search Report and Written Opinion, mailed Nov. 28, 2018.
International Preliminary Report on Patentability for corresponding International Application No. PCT/US2018/052215, Apr. 2, 2020.
Kanashiro-Takeuchi et al., Activation of growth hormone releasing hormone (GHRH) receptor stimulates cardiac reverse remodeling after myocardial infarction (MI), Proc. Natl. Acad. Sci. USA., 109:559-63 (2011).
Kanashiro-Takeuchi et al., Cardioprotective effects of growth hormone-releasing hormone agonist after myocardial infarction, Proc. Natl. Acad. Sci. USA., 107(6):2604-2609 (2010).

(Continued)

*Primary Examiner* — Taeyoon Kim
*Assistant Examiner* — Jianjian Zhu
(74) *Attorney, Agent, or Firm* — MARSHALL, GERSTEIN & BORUN LLP (57) ABSTRACT

The disclosure provides a method of obtaining a population of cardiomyogenic precursor cells. The method comprises (a) differentiating induced pluripotent stem cells (iPSCs) to iPSC-derived cardiac precursor cells; and (b) isolating cardiac precursor cells expressing mammalian growth hormone-releasing hormone receptor (GHRHR) to obtain a population of iPSC-derived cardiomyogenic precursor cells.

4 Claims, 3 Drawing Sheets

Specification includes a Sequence Listing.

(56) References Cited

OTHER PUBLICATIONS

Kanashiro-Takeuchi et al., New therapeutic approach to heart failure due to myocardial infarction based on targeting growth hormone-releasing hormone receptor, Oncotarget., 6(12):9728-9739 (2015).
Karantalis et al., Synergistic Effects of Combined Cell Therapy for Chronic Ischemic Cardiomyopathy, J. Am. Coll. Cardiol., 66(18):1990-1999 (2015).
Kempf et al., Controlling expansion and cardiomyogenic differentiation of human pluripotent stem cells in scalable suspension culture, Stem Cell Reports, 3(6):1132-1146 (2014).
Lalit et al., Induced pluripotent stem cells for post-myocardial infarction repair: remarkable opportunities and challenges, Circ. Res., 114:1328-1345 (2014).
Thiriet, M, Coronary Artery Disease and Myocardial Infarction. Diseases of the Cardiac Pump, p. 379-471, Switzerland: Springer International Publishing (2015).
NCT02501811, Combination of Mesenchymal and C-kit+ Cardiac Stem Cells as Regenerative Therapy for Heart Failure (CONCERT-HF), The University of Texas Health Science Center, Houston, first posted Jul. 17, 2015.
Shiba et al., Cardiac applications for human pluripotent stem cells, Curr. Pharm. Des., 15(24):2791-2806 (2009).

\* cited by examiner

METHODS FOR OBTAINING CARDIOMYOGENIC PRECURSOR CELLS

CROSS-REFERENCE TO RELATED APPLICATIONS

This application is a U.S. National Phase of International Patent Application No. PCT/US2018/052215 filed on Sep. 21, 2018, which claims priority to U.S. Provisional Patent Application No. 62/562,150, filed on Sep. 22, 2017, the disclosure of which is hereby incorporated by reference in its entirety.

STATEMENT OF U.S. GOVERNMENTAL INTEREST

This invention was made with government support under grant numbers HL107110 HL084275, HL094848, and HL113460 awarded by the National Institutes of Health (NIH) and National Heart, Lung, and Blood Institute (NHLBI). The government has certain rights in this invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 51287_Seq-listing.K Size: 4,967 bytes; Created: Sep. 21, 2018.

FIELD OF THE INVENTION

The disclosure relates to methods of obtaining cardiomyogenic precursor cells.

BACKGROUND

Heart disease accounts for 1 in 3 deaths worldwide, largely due to the limited ability of adults to regenerate heart muscle cells in response to damage. Current medical solutions involve surgical intervention and/or lifelong disease management with pharmacologic agents, such as β-blockers, ACE inhibitors and statins. Novel therapeutic approaches are needed to improve clinical outcomes, reduce treatment duration and limit cost of cardiovascular disease. A promising medical strategy involves induced pluripotent stem cell (iPSC)-based cell therapeutics. iPSCs are a novel regenerative medical tool derived from adult cells through genetic reprogramming, which does not require embryo destruction. Use of iPSCs in clinical practice is hampered by a number of challenges. The development of clinical-grade iPSC-based products requires prior manufacturing of iPSCs from genomic and karyotype stable somatic cells, as well as burdensome steps to minimize the risk of tumorigenicity. There remains a need for an efficient method of generating stem cell-based compositions suitable, e.g., for therapeutic applications.

SUMMARY

The disclosure is directed to a method of obtaining cardiomyogenic precursor cells. The method comprises differentiating induced pluripotent stem cells (iPSCs) to cardiac precursor cells (e.g., culturing the iPSCs in differentiation medium for a time period of up to 7 days), and isolating cardiac precursor cells expressing mammalian growth hormone-releasing hormone receptor (GHRHR) to obtain a population of cardiomyogenic precursor cells. In various aspects, the isolation step is performed using flow-cytometry or magnetic cell-sorting.

In various aspects, the method further comprises, prior to the differentiation step, culturing a population of iPSCs to expand the iPSC population. Optionally, the differentiation step comprises treating the iPSCs with a glycogen synthase kinase 3 (GSK3) inhibitor, a Wnt inhibitor, somatostatin and recombinant growth hormone releasing hormone (or synthetic analogs of any of the foregoing).

In various embodiments, the method further comprises selecting for c-Kit negative cardiac precursor cells. In some aspects, the isolated iPSC-derived cardiomyogenic precursor cells express nuclear homeobox transcription factors, NK2 Homeobox 5 (Nkx2.5) and Isl1.

The disclosure also provides a population of iPSC-derived cardiomyogenic precursor cells produced by the method described herein. The disclosure further provides a method of treating a cardiac disorder, the method comprising administering to a subject in need thereof the population of iPSC-derived cardiomyogenic precursor cells. The cardiac disorder is, for example, myocardial infarction, angina, congenital heart disease, ischemic or non-ischemic heart failure, heart failure with or without preserved ejection fraction, or dilated cardiomyopathy.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. In addition, the invention includes, as an additional aspect, all embodiments of the invention narrower in scope in any way than the variations specifically mentioned above. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

DETAILED DESCRIPTION

The disclosure relates to methods of obtaining cardiomyogenic precursor cells from iPSCs. This disclosure is the first to utilize the cell-surface molecule, growth hormone-releasing hormone receptor (GHRHR), to isolate cardiomyogenic precursor cells from iPSCs and other cardiac precursor cells. Previous studies utilized adult cardiac stem cells (Florea et al., Circulation Research. 2014; 115:A244; Shiba et al., Curr Pharm Des. 2009; 15(24):2791-2806) which express c-Kit, a marker of cardiac neural crest (CNC) cells but not cardiac mesoderm progenitors (Hatzistergos et al., Proc Natl Acad Sci USA 2015; 112(42):13051-6). In contrast, the method of the disclosure allows isolation of cardiomyogenic cardiac precursor cells, which represent a distinct, immature cell population having the ability to develop into cardiomyocytes. In various embodiments, the isolated iPSC-derived cardiomyogenic precursor cells are c-Kit negative. The method of the disclosure allows collection of potentially unlimited quantities of cardiomyogenic precursor cells.

In one aspect, the disclosure provides a method of obtaining cardiomyogenic precursor cells from iPSCs. The method comprises (a) differentiating iPSCs to cardiac precursor cells. The iPSCs may be human (hiPSCs) or porcine (piPSCs) or any other mammalian species in origin. Cardiac precursor cells are stem cells with the potential to differentiate into multiple cardiac cell types. Cardiomyogenic precursor cells are a subset of cardiac precursor cells with the ability to differentiate into a population of beating cardiomyocytes. Methods of differentiating iPSCs to cardiac precursor cells are known in the art. In various aspects of the method, the iPCSs are treated with a glycogen synthase kinase 3 (GSK3) inhibitor, a Wnt inhibitor, somatostatin and recombinant growth hormone releasing hormone (or synthetic analogs of any of the foregoing) to differentiate iPCSs to cardiac precursor cells. Optionally, the iPSCs are cultured for a time period of up to 7 days under conditions that promote differentiation of the iPSCs into cardiac precursor cells (e.g., 1, 2, 3, 4, 5, 6, or 7 days). Also optionally, the method comprises culturing a population of iPSCs to expand the iPSC population prior to step (a).

The method further comprises (b) isolating cardiac precursor cells expressing GHRHR to obtain a population of iPSC-derived cardiomyogenic precursor cells. Growth hormone-releasing hormone (GHRH) is a highly versatile signaling molecule that exerts a broad range of regulatory influences in the cardiovascular system. The receptor for GHRH, GHRHR, is a G-protein-coupled receptor. The amino acid sequence of human GHRHR is provided as SEQ ID NO: 1. In various aspects, cells expressing GHRHR are separated by undesired cells (i.e., cardiac precursor cells not expressing GHRHR) using flow-cytometry or magnetic cell-sorting.

In various embodiments, the method further comprises a negative selection step to isolate cells which do not express the marker c-kit. Put another way, c-kit-positive cells are optionally removed from the cell population in step (b) to obtain a population of cells that are c-kit-negative. In various aspects, c-kit cardiomyogenic precursor cells are isolated using flow-cytometry, or magnetic cell-sorting is employed to remove c-kit$^+$ cells. In some aspects, the resulting cell population from step (b) expresses nuclear homeobox transcription factors, Nkx2.5 and Isl1 Nkx2.5 is a master regulator gene of the cardiac lineage (Behrens et al., Stem Cells Dev. 2013; 22(15): 2211-2220). In various aspects, step (b) further comprises screening cells for expression of Nkx2.5 and Isl1 to obtain a population of cells that express Nkx2.5 and Isl1 in combination with GHRHR.

In further embodiments, the disclosure provides a population of iPSC-derived cardiomyogenic precursor cells isolated using the method described herein. Also provided is a method of treating a cardiac disorder (which may be congenital and/or adult) comprising administering the population of iPSC-derived cardiomyogenic precursor cells to a mammalian subject (e.g., a human subject) in need thereof. In related embodiments, the cardiac disorder is, for example, congenital heart disease, angina, myocardial infarction, ischemic or non-ischemic heart failure, heart failure with or without preserved ejection fraction, or dilated cardiomyopathy.

The population of iPSC-derived cardiomyogenic precursor cells may be administered via any suitable route of administration which results in delivery to cardiac tissue. For example. in various embodiments, the population of iPSC-derived cardiomyogenic precursor cells are surgically implanted in cardiac tissue. Alternatively, the route of administration is catheter-based, for example, intravenous infusion or intracoronary infusion. In various aspects, the population of iPSC-derived cardiomyogenic precursor cells is delivered via intramyocardial injection. Optionally, the population of iPSC-derived cardiomyogenic precursor cells is administered (e.g., infused or injected) or applied topically to cardiac tissue during surgery. The aforementioned routes of administration are exemplary and not meant to be limiting; other routes of administration are also contemplated (e.g., systemic, parenteral, or intravenous) optionally in connection with implants, reservoirs, or slow release formulations.

The iPSC-derived cardiomyogenic precursor cell population is, in various aspects, autologous or allogeneic to the recipient. The amount of iPSC-derived cardiomyogenic precursor cell administered is that which achieves a desired effect, i.e., to ameliorate, prevent or improve an unwanted condition, disorder, or symptom of the subject, in an appropriate time frame. The population (or dose) of iPSC-derived cardiomyogenic precursor cells comprises, for example, $10 \times 10^1$-$10 \times 10^9$ cells, delivered in a single administration or multiple administrations per dose. In related embodiments, the iPSC-derived cardiomyogenic precursor cell population is provided as a stand-alone treatment. Alternatively, the iPSC-derived cardiomyogenic precursor cell population is administered as part of a treatment regimen which also includes, for instance, standard-of-care therapies or other cell-, drug- and gene-based therapies.

The disclosure provides a physiologically acceptable (e.g., pharmaceutically acceptable) composition comprising a population of iPSC-derived cardiomyogenic precursor cells and physiologically acceptable excipient(s). Compositions suitable for administration typically include sterile aqueous solutions or dispersions and lyophilized compositions for reconstitution into sterile injectable solutions or dispersions. Typical excipients, diluents, additives, or carriers include, but are not limited to, sterile water, physiological saline or other salt solutions, sugars such as glucose, wetting or emulsifying agents, pH buffering agents, viscosity modifiers, preservatives, and the like.

In one aspect, the method further comprises administering a GHRHR agonist with the population iPSC-derived cardiomyogenic precursor cells. The GHRHR agonist may be present in same composition as the population of cells or may be administered in a separate composition. If administered in a separate composition, the GHRHR agonist may be administered shortly before administration of the population of cells (e.g., within 6 hours, within 4 hours, within 2 hours, within 1 hour, within 30 minutes, within 15 minutes, or within 5 minutes of administration of the population of cells), substantially simultaneous with the administration of the population of cells, or shortly after the population of cells (e.g., within 6 hours, within 4 hours, within 2 hours, within 1 hour, within 30 minutes, within 15 minutes, or within 5 minutes of administration of the population of cells). Alternatively, the GHRHR agonist may be administered after (or before) a longer period of time with respect to the population of cells (e.g., 12 14, or 48 hours before/after administration of the population of cells). Examples of GHRHR agonists include, but are not limited to, CJC-1295, dumorelin, somatorelin, rismorelin, sermorelin, tesamorelin, or GHRH-A (JI-38), or combinations thereof.

In one aspect, the population of iPSC-derived cardiomyogenic precursor cells are modified to increase GHRHR or GHRH protein levels. The sequence of GHRH is provided as SEQ ID NO: 2. Introduction of nucleic acid into host cells to produce a target protein, e.g., GHRHR or GHRH, is well understood in the art. Exogenous nucleic acid may be introduced into host cells via, e.g., expression vector (e.g., viral or non-viral vectors), non-vector based methods (e.g., using naked DNA or DNA complexes), or a combination thereof. Suitable viral vectors include, but are not limited to, retroviral vectors, herpes simplex virus (HSV)-based vectors, parvovirus-based vectors, e.g., adeno-associated virus (AAV)-based vectors, AAV-adenoviral chimeric vectors, and adenovirus-based vectors. Other means of facilitating nucleic acid delivery to host cells include, e.g., yeast systems, particle bombardment, nanoparticle-mediated uptake, liposomes, microvesicles, and hydrodynamic-based gene delivery.

The disclosure contemplates both therapeutic and/or prophylactic treatment, as appropriate. It will be appreciated that "treating a cardiac disorder" does not require complete amelioration of the disorder; any improvement in a symptom or manifestation of the disorder confers a beneficial effect on the subject. Methods for measuring cardiac function (e.g., contractile function) are known in the art and are described, for example, in the Textbook of Medical Physiology, Tenth edition, (Guyton et al., W.B. Saunders Co., 2000). For example, cardiac ejection can be monitored using, e.g., echocardiography, nuclear or radiocontrast ventriculography, or magnetic resonance imaging. Other measures of cardiac function include, but are not limited to, myocardial contractility, resting stroke volume, resting heart rate, resting cardiac index, Doppler imaging, cardiovascular performance during stress/exercise. Optionally, cardiac function is increased by at least 5%, 10%, 15%, 20%, 25%, 30%, 40%, 50%, 60%, 70%, 80%, 90%, or even 100% relative to the cardiac function prior to treatment.

In jurisdictions that forbid the patenting of methods that are practiced on the human body, the meaning of "administering" of a composition to a human subject may be restricted to prescribing a controlled substance that a human subject can self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

Example 1: GHRHR is Universally Expressed by NKX2.5/ISL1+ Cardiac Precursor Cells and Cardiomyocytes of Both Mesoderm and CNC Origin Temporal analysis of GHRHR expression was performed in an in-vitro model of human cardiogenesis using induced hiPSCs (hiPSCs) and SOX10::GFP embryonic stem cells (hESCs); and mouse (in-vivo) cardiogenesis in wild-type (VVT), MEF2c-AHF-Cre, Wnt1-Cre2 and ckit-CreERT2/+ 4− reporter mice.

Gene expression and confocal immunofluorescence analyses during chemically-defined, stage-specific, cardiac lineage differentiation indicated that GHRHR is not expressed in undifferentiated hiPSCs or during specification into primitive streak-like Brachyury+ or Mesp1 precardiac cells; but is induced in cardiogenic mesoderm-like cells, at the stage of commitment into NKX2.5+ and/or ISL1+ CPCs (p=0.001) and persists in Troponin-T+ cardiomyocytes. Similarly, experiments modeling cardiac neural crest (CNC) with SOX10::GFP hESCs indicated that GHRHR is not expressed by GFP+ CNCs but is induced following differentiation into NKX2.5+ and/or ISL1+ derivatives. Importantly, stimulation with 1 µM recombinant GHRH during days 5-7 of hiPSCs differentiation increased NKX2.5 expression 2.5-fold, an effect that was abolished by exposure to 1 µM Somatostatin, a GHRH antagonist (p=0.0009). FIGS. 1A-1E show temporal gene-expression analyses in an iPSC model of human cardiomyogenesis, illustrating that GHRH and GHRHR are specifically induced on day 7, following commitment of Brachyury+ precardiac cells into NKX2.5 and ISL1 cardioblasts. Last, in vivo analyses in VVT, MEF2c-AHF-Cre, Wnt1-Cre2 and cKit-CreERT2/+ reporter embryonic and postnatal hearts corroborated that GHRHR specifically marks NKX2.5+ mesoderm- and CNC-lineage descendants in vivo, whereas GHRHR is not expressed by Wnt1-Cre2 and cKit-CreERT2/+ CNCs descendants that are NKX2.5− (NKX2.5-negative).

Together these findings indicate that GHRHR is expressed by NKX2.5+ISL1+ cardiac precursor cells and cardiomyocytes of both mesoderm and CNC origin.

Example 2: Derivation of GHRHR+ Cardiomyoblasts from PSCs

To generate GHRHR+ cardiomyoblasts, feeder-free human pluripotent stem cells (hPSCs) were grown in monolayers. At 60-90% confluency (Day 0), the PSC medium was changed to RPM11640 (Thermo Scientific), supplemented with B-27 minus insulin (Thermo Scientific) and 6 µM of the GSK3 inhibitor Chir99021 (Tocris). On day 2, medium was changed to RPMI with B-27 minus insulin (M1). On day 3, M1 medium was supplemented with 5 µM of the Wnt inhibitor IWP2 or IWR1, for 48 h. On day 5, and every other day thereafter, the medium was replenished with fresh M1. On days 8-10, selection of GHRHR+ cardiomyoblasts was performed as follows. Differentiated PSC cultures are pre-treated for 1 hour with 10 µM of the RHO/ROCK inhibitor Y-27632, dissolved in M1. Cells were rinsed with PBS and dissociated into single-cell suspension with trypLE select. Enrichment of GHRHR+ cells was performed via flow-cytometry or magnetic cell-sorting using a GHRHR antibody (Abcam ab28692). The positive fraction was resuspended in M1 and cryopreserved.

Example 3: Use of iPSC-Derived GHRHR+ CPCs for the Treatment of Adult and Congenital Heart Diseases The method described herein re-derives highly pure, clinical-grade Nkx2.5+/Isl1+ cardiomyocyte progenitor cells from iPSCs. The method minimizes oncologic and arrhythmogenic risks associated with use of stem cell therapy, because the iPSCs can be derived from clinically safe MSCs, and iPSC-derived cardiomyocyte progenitor cells are selected from unwanted iPSC derivatives, optionally ~24 hours prior to their terminal differentiation into beating cardiomyocytes, with a novel, antibody-based selection step for GHRHR.

Stem cells are injected into a subject requiring cardiac intervention in a number of ways including, but not limited to, intramuscular (trans-catheter, direct injection), intracoronary (with or without using the stop-flow technique), intravenous, intramyocardial, surgical, catheter, epicardial placement, and retrograde intracoronary sinus administration. However, despite the low engraftment rate, direct intramyocardial injection with cardiac mapping is a preferred method, as it is directed at the border zone of the scar and it receives the highest concentration of cells in a targeted location.

Mortality status-post MI remains high and those who progress to HF have a 20-30 percent chance of death within the year despite standard pharmacological therapy. In combination with standard medical therapy, stem cell therapy will aid in the healing process by salvaging ischemic tissue in the subacute setting, thus reducing the proarrhythmic focus and subsequent mortality rate. The inflammatory milieu after an MI is hostile to native stem cells and cardiomyocytes alike. iPSCs can be introduced at, e.g., two weeks after the event, at which time the autologous cells will have had time to replicate and the inflammation will have begun subsiding. Subjects with congenital heart diseases, chronic ischemic HF, HF with preserved ejection fraction and dilated cardiomyopathy are contemplated as recipients of the population of IPSC-derived cardomyocyte progenitor cells of the disclosure.

Figure 1A:
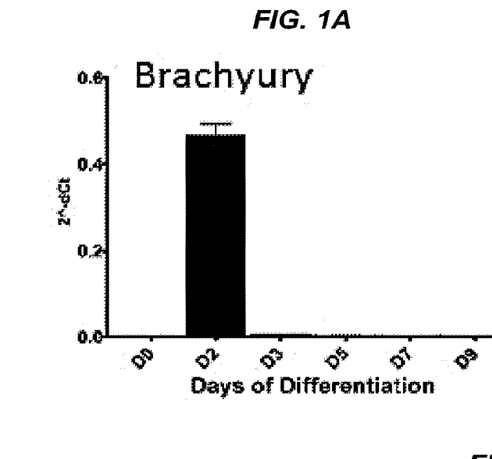
FIGS. 1A-1E depict temporal gene-expression analyses in an iPSC model of human cardiomyogenesis, illustrating that growth hormone-releasing hormone (GHRH) and growth hormone-releasing hormone receptor (GHRHR) are specifically induced on day 7, following commitment of Brachyury[+] precardiac cells into NKX2.5 and ISL1 cardioblasts.
Figure 1B:
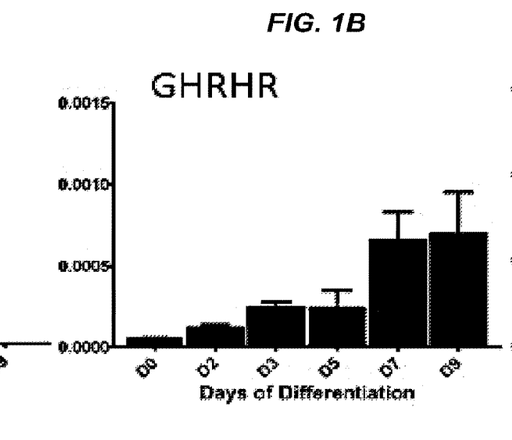
Figure 1C:
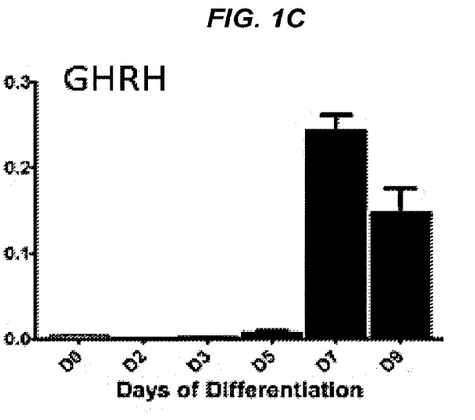
Figure 1D:
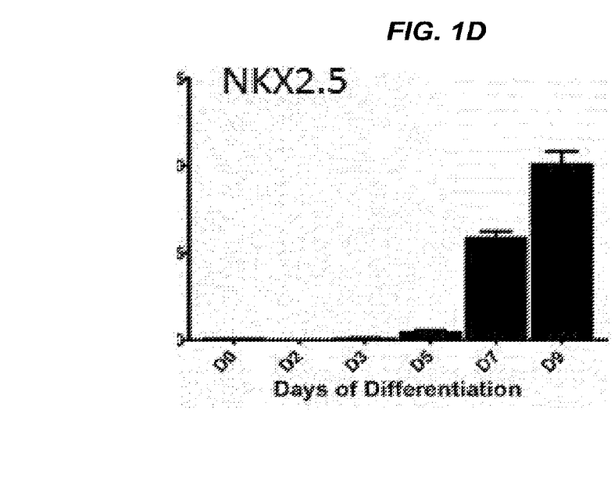
Figure 1E:
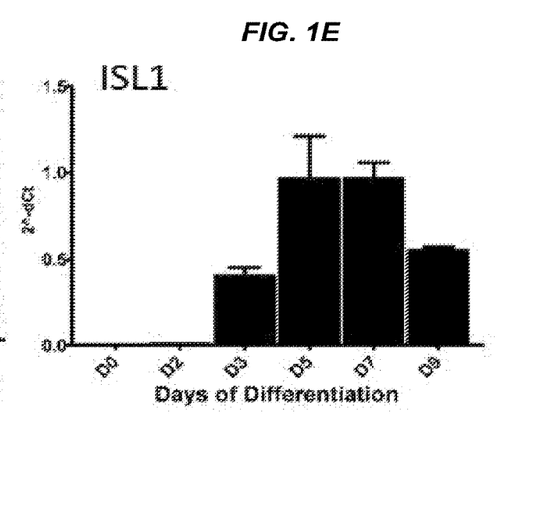
Figure 2A:
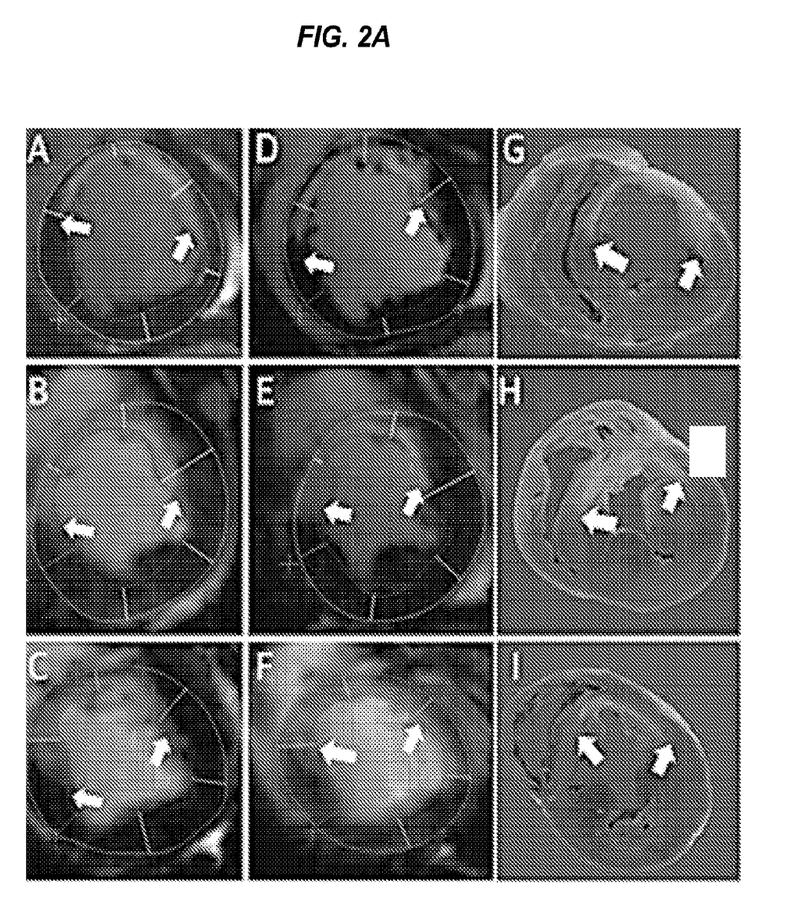
FIGS. 2A-2C are representative examples on the assessment of anti-fibrotic effects of cell therapy in pigs with myocardial infarction, using cardiac MRI.
Figure 2B:
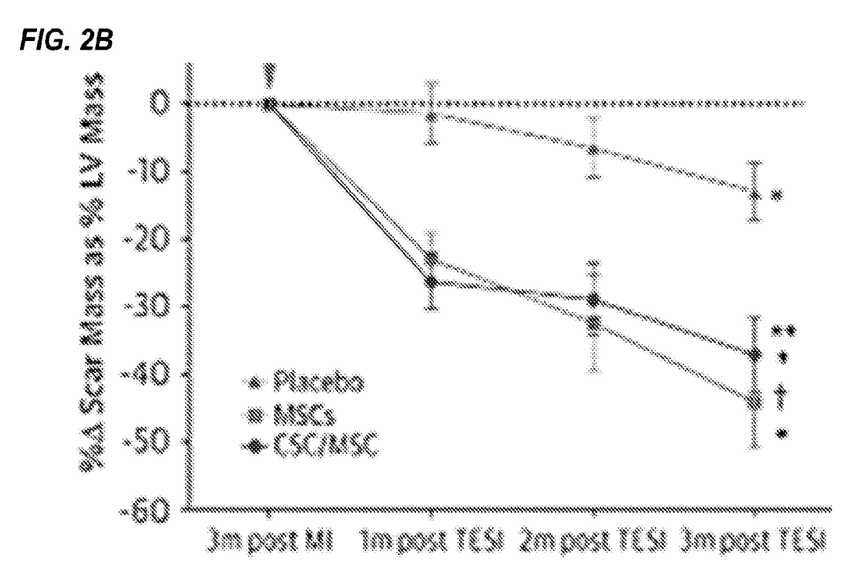
Figure 2C:
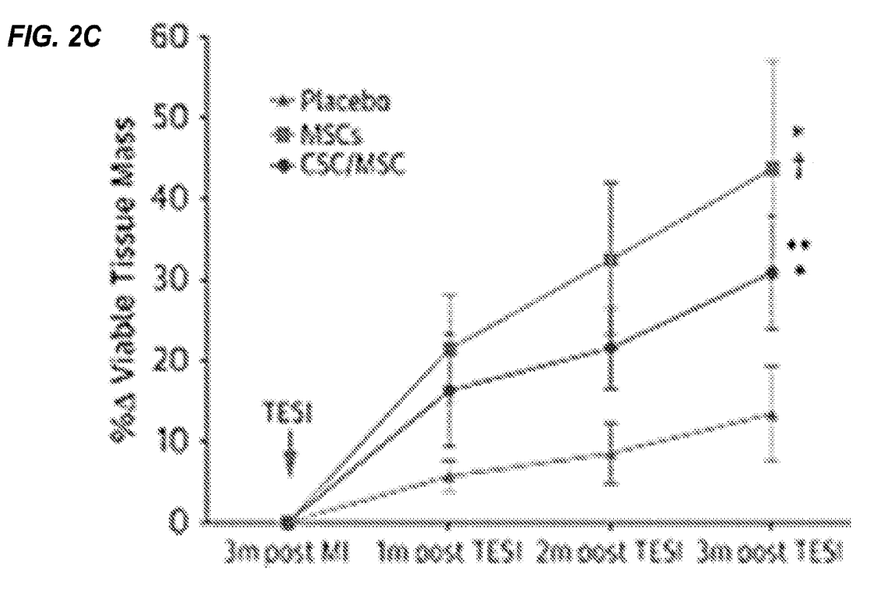

A head-to-head placebo-controlled comparison of GHRHR-sorted porcine iPSCs (piPSC)-derived cardiac progenitor cells with their parent porcine MSC line and unsorted piPSCs (Day 7 of cardiac differentiation) in a sex-mismatched porcine model of cell therapy in response to (sub)acute myocardial infarction (MI), will be performed. FIG. 2 shows examples of a recent study, in which this animal model was utilized to test the safety and efficacy of a combination cell therapy, with adult cardiac stem cells and mesenchymal stem cells (MSCs) (Karantalis et al., J Am Coll Cardiol. 2015; 66(18):1990-9). The results from this study led to IND approval for the CONCERT-HF clinical trial (ClinicalTrials.gov Identifier: NCT02501811).

The goal of the study is to confirm the safety and efficacy of the use of iPSC-derived GHRHR+ cardiomyocyte progenitor cells in the treatment of adult and congenital heart diseases. The porcine model of experimental MI will be employed to perform a sex-mismatched, placebo-controlled, double-blinded, dose-response comparison of porcine iPSC-derived GHRHR+ cardiomyocyte progenitor cells, with their parent MSC product and iPSC-derived cells without GHRHR sorting. Treatment will be delivered in a blinded fashion, via transendocardial stem cell injection (TESI) as previously described (Karantalis et al., J Am Coll Cardiol. 2015; 66(18):1990-9). Infarcted animals will be randomized to receive 5, 25 or 100×10$^6$ male iPSC-derived cardiomyocyte progenitor cells, 100×10$^6$ male MSCs from which the iPSC-cardiomyocyte progenitor cells were derived, 100×10$^6$ unsorted male piPSCs derivatives or placebo. Animals will be followed for 3 months prior to euthanasia. A complete necropsy will be performed and tissues inspected for ectopic tissue formation by a trained veterinary pathologist.

Populations of 6.5×10$^8$ cGLP-grade GHRHR+ cardiomyocyte progenitor cells and 5×10$^8$ cGLP-grade iPSC derivatives not sorted for GHRHR will be produced. The two iPSC-based cell products will be derived from a single male, porcine iPSC line, which were generated from MSCs under feeder-free, virus-free, transgene-free, chemically defined conditions. In addition, cryopreserved 1×10$^9$ cells from the same MSC line will be used as the current standard in cell-based therapy for heart disease, in head-to-head comparison with their iPSC derivatives.

The procurement of 30 female Yorkshire swine and induction of experimental myocardial infarction will be performed. Animals will undergo closed-chest ischemic reperfusion myocardial infarction (MI), in which MI is induced by inflation of a coronary angioplasty balloon in the mid left anterior descending (LAD) artery for 90 minutes as previously described (Karantalis etal, J Am Coll Cardiol. 2015; 66(18):1990-9). The following safety endpoints will be recorded before and after MI: survival; body weights; continuous cardiac rhythm monitoring for ventricular or supraventricular arrhythmias using implanted monitoring devices ("REVEAL DX 9528" and "REVEAL XT 9529" [Medtronic, Minneapolis, MN]); circulating blood markers (hematology, chemistry, and markers of cardiac injury CPK, CKMB, and Troponin I). Heart function is assessed with cardiac MRI using a 3.0T clinical MR scanner (Magnetom, Siemens).

Randomized, double-masked, placebo-controlled, preclinical studies also will be performed. This study entails the randomization of the MI animals in the following 6 TESI groups (5 animals/group): 5, 25 or 100×10$^6$ male iPSC-derived CPCs, 100×10$^6$ male MSCs from which the iPSC-CPCs were derived, 100×10$^6$ unsorted male piPSCs derivatives, or placebo (plasmalyte). TESI is performed with the NOGA myostar catheter under the NOGA electromechanical mapping system. Animals are followed for 3 months following therapy for safety and efficacy endpoints.

To assess safety and efficacy endpoints, animals are euthanized 3 months after TESI, and safety and efficacy endpoints are analyzed in a blinded manner. In addition, gross and microscopic tissue analysis from brain, liver, spleen, kidney, lung and ileum for the presence of neoplastic tissue will be performed at the end of the study. Furthermore, the engraftment of allografts will be evaluated based on the detection of Y-chromosome with Fluorescent In Situ Hybridization as previously described (Karantalis etal, J Am Coll Cardiol. 2015; 66(18):1990-9).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A method of obtaining a population of human cardiomyogenic precursor cells, the method comprising:
   (a) differentiating human induced pluripotent stem cells (hiPSCs) in the presence of all of a glycogen synthase kinase 3 (GSK3) inhibitor, a Wnt inhibitor, and recombinant growth hormone releasing hormone or their synthetic analogs to obtain hiPSC-derived human cardiac precursor cells; and
   (b) isolating a population of human cardiac precursor cells based on (i) expression of human growth hormone-releasing hormone receptor (GHRHR) using a GHRHR antibody and (ii) no expression of c-Kit to obtain a population consisting essentially of hiPSC-derived human cardiomyogenic precursor cells which express Nkx2.5 and Isl1.

2. The method of claim 1, further comprising, prior to step (a), culturing a population of hiPSCs to expand the iPSC population.

3. The method of claim 1, wherein step (a) is performed for a time period of up to 7 days.

4. The method of claim 1, wherein step (b) is performed using flow-cytometry or magnetic cell-sorting.

* * * * *

SEQUENCE LISTING

<160> NUMBER OF SEQ ID NOS: 2

<210> SEQ ID NO 1
<211> LENGTH: 423
<212> TYPE: PRT
<213> ORGANISM: Homo sapiens
<220> FEATURE:
<221> NAME/KEY: MISC_FEATURE
<223> OTHER INFORMATION: GHRH receptor

<400> SEQUENCE: 1

```
Met Asp Arg Arg Met Trp Gly Ala His Val Phe Cys Val Leu Ser Pro
1               5                   10                  15

Leu Pro Thr Val Leu Gly His Met His Pro Glu Cys Asp Phe Ile Thr
            20                  25                  30

Gln Leu Arg Glu Asp Glu Ser Ala Cys Leu Gln Ala Ala Glu Glu Met
        35                  40                  45

Pro Asn Thr Thr Leu Gly Cys Pro Ala Thr Trp Asp Gly Leu Leu Cys
    50                  55                  60

Trp Pro Thr Ala Gly Ser Gly Glu Trp Val Thr Leu Pro Cys Pro Asp
65                  70                  75                  80

Phe Phe Ser His Phe Ser Ser Glu Ser Gly Ala Val Lys Arg Asp Cys
                85                  90                  95

Thr Ile Thr Gly Trp Ser Glu Pro Phe Pro Pro Tyr Pro Val Ala Cys
            100                 105                 110

Pro Val Pro Leu Glu Leu Leu Ala Glu Glu Glu Ser Tyr Phe Ser Thr
        115                 120                 125

Val Lys Ile Ile Tyr Thr Val Gly His Ser Ile Ser Ile Val Ala Leu
    130                 135                 140

Phe Val Ala Ile Thr Ile Leu Val Ala Leu Arg Arg Leu His Cys Pro
145                 150                 155                 160

Arg Asn Tyr Val His Thr Gln Leu Phe Thr Thr Phe Ile Leu Lys Ala
                165                 170                 175

Gly Ala Val Phe Leu Lys Asp Ala Ala Leu Phe His Ser Asp Asp Thr
            180                 185                 190

Asp His Cys Ser Phe Ser Thr Val Leu Cys Lys Val Ser Val Ala Ala
        195                 200                 205

Ser His Phe Ala Thr Met Thr Asn Phe Ser Trp Leu Leu Ala Glu Ala
    210                 215                 220

Val Tyr Leu Asn Cys Leu Leu Ala Ser Thr Ser Pro Ser Ser Arg Arg
225                 230                 235                 240

Ala Phe Trp Trp Leu Val Leu Ala Gly Trp Gly Leu Pro Val Leu Phe
                245                 250                 255

Thr Gly Thr Trp Val Ser Cys Lys Leu Ala Phe Glu Asp Ile Ala Cys
            260                 265                 270

Trp Asp Leu Asp Asp Thr Ser Pro Tyr Trp Trp Ile Ile Lys Gly Pro
        275                 280                 285

Ile Val Leu Ser Val Gly Val Asn Phe Gly Leu Phe Leu Asn Ile Ile
    290                 295                 300

Arg Ile Leu Val Arg Lys Leu Glu Pro Ala Gln Gly Ser Leu His Thr
305                 310                 315                 320

Gln Ser Gln Tyr Trp Arg Leu Ser Lys Ser Thr Leu Phe Leu Ile Pro
                325                 330                 335

Leu Phe Gly Ile His Tyr Ile Ile Phe Asn Phe Leu Pro Asp Asn Ala
            340                 345                 350
```

```
Gly Leu Gly Ile Arg Leu Pro Leu Glu Leu Gly Leu Gly Ser Phe Gln
            355                 360                 365

Gly Phe Ile Val Ala Ile Leu Tyr Cys Phe Leu Asn Gln Glu Val Arg
    370                 375                 380

Thr Glu Ile Ser Arg Lys Trp His Gly His Asp Pro Glu Leu Leu Pro
385                 390                 395                 400

Ala Trp Arg Thr Arg Ala Lys Trp Thr Thr Pro Ser Arg Ser Ala Ala
                405                 410                 415

Lys Val Leu Thr Ser Met Cys
            420

<210> SEQ ID NO 2
<211> LENGTH: 108
<212> TYPE: PRT
<213> ORGANISM: Homo sapiens

<400> SEQUENCE: 2

Met Pro Leu Trp Val Phe Phe Phe Val Ile Leu Thr Leu Ser Asn Ser
1               5                   10                  15

Ser His Cys Ser Pro Pro Pro Leu Thr Leu Arg Met Arg Arg Tyr
                20                  25                  30

Ala Asp Ala Ile Phe Thr Asn Ser Tyr Arg Lys Val Leu Gly Gln Leu
            35                  40                  45

Ser Ala Arg Lys Leu Leu Gln Asp Ile Met Ser Arg Gln Gln Gly Glu
        50                  55                  60

Ser Asn Gln Glu Arg Gly Ala Arg Ala Arg Leu Gly Arg Gln Val Asp
65                  70                  75                  80

Ser Met Trp Ala Glu Gln Lys Gln Met Glu Leu Glu Ser Ile Leu Val
                85                  90                  95

Ala Leu Leu Gln Lys His Ser Arg Asn Ser Gln Gly
            100                 105
```